(12) United States Patent
Purdy et al.

(10) Patent No.: US 11,760,720 B2
(45) Date of Patent: Sep. 19, 2023

(54) MODIFIED SULFURIC ACID AND USES THEREOF

(71) Applicant: SixRing Inc., Calgary (CA)

(72) Inventors: Clay Purdy, Medicine Hat (CA); Markus Weissenberger, Calgary (CA); Kyle G. Wynnyk, Calgary (CA); Karl W. Dawson, Calgary (CA)

(73) Assignee: SixRing Inc.

( * ) Notice: Subject to any disclaimer, the term of this patent is extended or adjusted under 35 U.S.C. 154(b) by 108 days.

(21) Appl. No.: 17/187,247

(22) Filed: Feb. 26, 2021

(65) Prior Publication Data

US 2021/0269394 A1  Sep. 2, 2021

(30) Foreign Application Priority Data

Feb. 28, 2020  (CA) ................................ CA 3074194

(51) Int. Cl.
| | | |
|---|---|---|
| *C01B 17/69* | (2006.01) | |
| *C07C 309/04* | (2006.01) | |
| *C07C 215/08* | (2006.01) | |
| *C07G 1/00* | (2011.01) | |
| *C01B 15/01* | (2006.01) | |
| *C07C 215/10* | (2006.01) | |
| *D21C 3/04* | (2006.01) | |
| *D21C 3/00* | (2006.01) | |
| *D21C 9/16* | (2006.01) | |

(52) U.S. Cl.
CPC ............ *C07C 309/04* (2013.01); *C01B 15/01* (2013.01); *C01B 17/69* (2013.01); *C07C 215/08* (2013.01); *C07C 215/10* (2013.01); *C07G 1/00* (2013.01); *D21C 3/006* (2013.01); *D21C 3/04* (2013.01); *D21C 9/16* (2013.01)

(58) Field of Classification Search
None
See application file for complete search history.

(56) References Cited

U.S. PATENT DOCUMENTS

| | | |
|---|---|---|
| 2,855,351 A | 10/1958 | Ermst |
| 4,626,319 A | 12/1986 | Kruger et al. |
| 4,756,845 A | 7/1988 | Sugawara et al. |
| 4,935,499 A * | 6/1990 | Ruske .................... D21H 21/28 162/162 |
| 5,080,756 A | 1/1992 | Kutney |
| 5,691,193 A | 11/1997 | Paice et al. |
| 5,955,050 A | 9/1999 | Drexler |
| 9,499,405 B2 | 11/2016 | Dindi |
| 9,890,321 B2 | 2/2018 | Shumway |
| 2003/0224960 A1* | 12/2003 | Scialla .................... D06L 4/13 510/312 |
| 2013/0156631 A1 | 6/2013 | Kumagai et al. |
| 2014/0113843 A1 | 4/2014 | Shumway |
| 2016/0021888 A1 | 1/2016 | Burke et al. |
| 2016/0074549 A1 | 3/2016 | Lei et al. |
| 2016/0264420 A1 | 9/2016 | Dindi |
| 2016/0298294 A1* | 10/2016 | Dietz ....................... D21C 9/10 |

FOREIGN PATENT DOCUMENTS

| | | |
|---|---|---|
| CA | 2134270 C | 7/2005 |
| CA | 2744569 A1 | 6/2010 |
| CA | 2923100 A1 | 9/2016 |
| CA | 2889135 C | 1/2018 |
| CN | 103572306 A | 2/2014 |
| CN | 103820796 A | 5/2014 |
| CN | 109761380 | * 5/2019 |
| CN | 109877097 A | 6/2019 |
| CN | 110485188 A | 11/2020 |
| EP | 0199385 A2 | 10/1986 |
| EP | 0779357 | * 12/1995 |
| JP | H07206804 A | 8/1995 |
| JP | 2010285697 | * 12/2010 |
| KR | 1920150114655 | 10/2015 |
| WO | 9612673 A1 | 5/1996 |
| WO | 2014065972 A1 | 5/2014 |

OTHER PUBLICATIONS

Rackemann et al., 2016 "The effect of pretreatment on methanesulfonic acid-catalyzed hydrolysis of bagasse to levulinic acid, formic acid, and furfural," RSC Advances 6(78):74525-35.
International Search Report from related Application No. PCT/CA2021/000017, dated Jun. 4, 2021 (4 pages).
U.S. Appl. No. 17/187,122, filed Feb. 26, 2021 (24 pages).
U.S. Appl. No. 17/187,354, filed Feb. 26, 2021 (18 pages).

* cited by examiner

*Primary Examiner* — Sheng H Davis
(74) *Attorney, Agent, or Firm* — Dechert LLP; Andrea L. C. Reid; Todd K. Macklin

(57) ABSTRACT

An aqueous composition comprising: sulfuric acid; a compound comprising an amine moiety; a compound comprising a sulfonic acid moiety; and a peroxide. Said composition being capable of delignifying biomass.

11 Claims, 1 Drawing Sheet

MODIFIED SULFURIC ACID AND USES THEREOF

1. FIELD OF THE INVENTION

Figure 1:
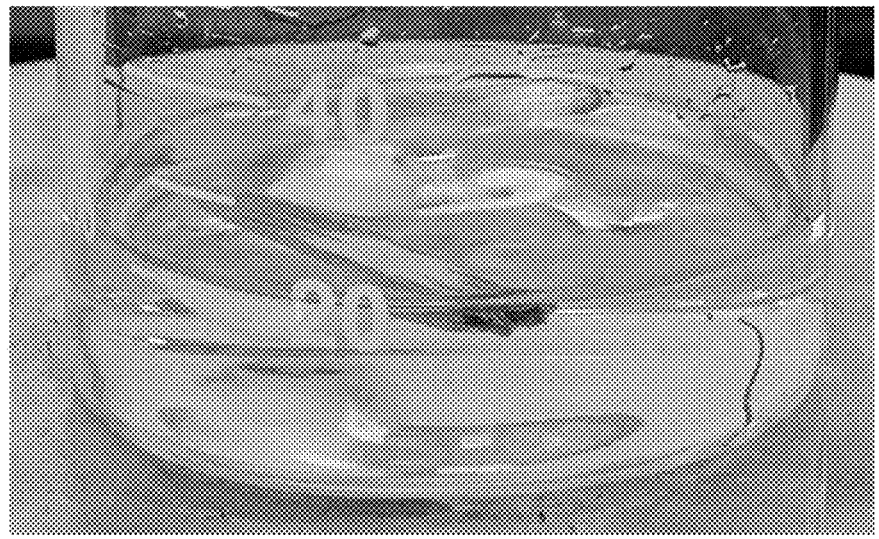

The present invention is directed to a method and composition useful in decomposing organic material such as biomass by oxidation such as, but not limited to, the delignification of biomass, as a broad example and more specifically, to a method and composition for performing such under more optimal conditions than those under which the kraft process is currently conducted.

2. BACKGROUND OF THE INVENTION

The first step in paper production and most energy-intensive one is the production of pulp. Notwithstanding water, wood and other plant materials used to make pulp contain three main components: cellulose fibers; lignin; and hemicelluloses. Pulping has a primary goal to separate the fibers from the lignin. Lignin is a three-dimensional polymer which figuratively acts as a mortar to hold all the fibers together within the plant. Its presence in finished pulp is undesirable and adds nothing to the finished product. Pulping wood refers to breaking down the bulk structure of the fiber source, be it chips, stems or other plant parts, into the constituent fibers. The cellulose fibers are the most desired component when papermaking is involved. Hemicellulose is a shorter branched carbohydrate polymer consisting of various sugar monomers which form a random amorphous polymeric structure. The presence of hemicellulose in finished pulp is not as critical to paper rigidity as cellulose is. This is also true for biomass conversion. The challenges are similar. Only the desired outcome is different. Biomass conversion would have the further breakdown to monocarbohydrates as a desired outcome while a pulp & paper process normally stops right after lignin dissolution.

There are two main approaches to preparing wood pulp or woody biomass: mechanical treatment and chemical treatment. Mechanical treatment or pulping generally consists of physically tearing the wood chips apart and, thus, tearing cellulose fibers apart in an effort to separate them from each other. The shortcomings of this approach include: broken or damaged cellulose fibers, thus shorter fibers; and lignin contamination or residue on the cellulose fibers, thus introducing or leaving behind impurities of the final product. This process also consumes large amounts of energy and is capital intensive due to the high pressure, corrosive chemicals and heat required. There are several approaches or processes included in chemical pulping. These are generally focused on the degradation the lignin and hemicellulose into, water-soluble molecules. These now degraded components are separated from the cellulose fibers by washing the latter without damaging the cellulose fibers. The chemical process is currently energy intensive as well, as high amounts of heat are typically required; and, in many cases, also require agitation or mechanical intervention adding inefficiencies and costs to the process.

There exist pulping or treatment methods which combine, to a various extent, the chemical aspects of pulping with the mechanical aspects of pulping. To name a few, one must consider include thermomechanical pulping (also commonly referred to as TMP), and chemithermomechanical pulping (CTMP). Through a selection of the advantages provided by each general pulping method, the treatments are designed to reduce the amount of energy required by the mechanical aspect of the pulping treatment. This can also directly impact the strength or tensile strength degradation of the fibers subjected to these combination pulping approaches. Generally, these approaches involve a shortened chemical treatment (compared to conventional exclusive chemical pulping) which is then typically followed by mechanical treatment to separate the fibers.

The most common process to make pulp for paper production is the kraft process. In the kraft process, wood chips are converted to wood pulp which is almost entirely pure cellulose fibers. The multi-step kraft process consists of a first step where wood chips are impregnated/treated with a chemical solution. This is done by soaking the wood chips and then pre-heating them with steam. This step swells the wood chips and expels the air present in them and replaces the air with the liquid. This produces black liquor a resultant by-product from the kraft process. It contains water, lignin residues, hemicellulose and inorganic chemicals. White liquor is a strong alkaline solution comprising sodium hydroxide and sodium sulfide. Once the wood chips have been soaked in the various chemical solutions, they undergo cooking. To achieve delignification in the wood chips, the cooking is carried out for several hours at temperatures reaching up to 176° C. At these temperatures, the lignin degrades to yield water soluble fragments. The remaining cellulosic fibers are collected and washed after the cooking step.

U.S. Pat. No. 5,080,756 teaches an improved kraft pulping process and is characterized by the addition of a spent concentrated sulfuric acid composition containing organic matter to a kraft recovery system to provide a mixture enriched in its total sulfur content that is subjected to dehydration, pyrolysis and reduction in a recovery furnace. The organic matter of the sulfuric acid composition is particularly beneficial as a source of thermal energy that enables high heat levels to be easily maintained to facilitate the oxidation and reduction reactions that take place in the furnace, thus resulting in the formation of sulfide used for the preparation of cooking liquor suitable for pulping.

Caro's acid, also known as peroxymonosulfuric acid ($H_2SO_5$), is one of the strongest oxidants known. There are several known reactions for the preparation of Caro's acid but one of the most straightforward involves the reaction between sulfuric acid ($H_2SO_4$) and hydrogen peroxide ($H_2O_2$). Preparing Caro's acid in this method allows one yield in a further reaction potassium monopersulfate (PMPS) which is a valuable bleaching agent and oxidizer. While Caro's acid has several known useful applications, one noteworthy is its use in the delignification of wood.

Biofuel production is another potential application for the kraft process. One of the current drawbacks of biofuel production is that it requires the use of food grade plant parts (such as seeds) in order to transform carbohydrates into fuel in a reasonably efficient process. The carbohydrates could be obtained from cellulosic fibers, by using non-food grade biomass in the kraft process; however, the energy intensive nature of the kraft process for delignification makes this a less commercially viable option. In order to build a plant based chemical resource cycle there is a great need for energy efficient processes which can utilize plant-based feedstocks that don't compete with human food production.

While the kraft pulping process is the most widely used chemical pulping process in the world, it is extremely energy intensive and has other drawbacks, for example, substantial odours emitted around pulp producing plants or general emissions that are now being highly regulated in many pulp and paper producing jurisdictions. In light of the current environmental challenges, economic challenges and climactic changes, along with emission fees being implemented, it is highly desirable to optimize the current pulping processes. In order to provide at least linear quality fibers without the current substantial detriment to the environment during the production thereof. Accordingly, there still exists a need for a composition capable of performing delignification on wood substance under reduced temperatures and pressures versus what is currently in use without requiring any additional capital expenditures.

3. SUMMARY OF THE INVENTION

According to an aspect of the present invention, there is provided an aqueous acidic composition comprising:
  sulfuric acid;
  a compound comprising an amine moiety;
  a compound comprising a sulfonic acid moiety; and
  a peroxide.

According to an aspect of the present invention, there is provided an aqueous acidic composition comprising:
  sulfuric acid;
  a compound comprising an amine moiety;
  a compound comprising a sulfonic acid moiety; and
wherein sulfuric acid and said compound comprising an amine moiety and said compound comprising a sulfonic acid moiety are present in a molar ratio of no less than 1:1:1.

Preferably, the sulfuric acid and said compound comprising an amine moiety and said compound comprising a sulfonic acid moiety are present in a molar ratio ranging from 28:1:1 to 2:1:1. More preferably, the sulfuric acid and said compound comprising an amine moiety and said compound comprising a sulfonic acid moiety are present in a molar ratio ranging from 24:1:1 to 3:1:1. Preferably, the sulfuric acid and said compound comprising an amine moiety and said compound comprising a sulfonic acid moiety are present in a molar ratio ranging from 20:1:1 to 4:1:1. More preferably, the sulfuric acid and said compound comprising an amine moiety and said compound comprising a sulfonic acid moiety are present in a molar ratio ranging from 16:1:1 to 5:1:1. According to a preferred embodiment of the present invention, the sulfuric acid and said compound comprising an amine moiety and said compound comprising a sulfonic acid moiety are present in a molar ratio ranging from 12:1:1 to 6:1:1.

According to a preferred embodiment of the present invention, said compound comprising an amine moiety and said compound comprising a sulfonic acid moiety are present in a molar ratio ranging from 2:1 to 1:2.

According to another preferred embodiment of the present invention, said compound comprising an amine moiety and said compound comprising a sulfonic acid moiety are present in a molar ratio ranging from 3:1 to 1:3.

According to a preferred embodiment of the present invention, said compound comprising an amine moiety and said compound comprising a sulfonic acid moiety are present in a molar ratio ranging from 4:1 to 1:4.

According to a preferred embodiment of the present invention, said compound comprising an amine moiety and said compound comprising a sulfonic acid moiety are present in a molar ratio ranging from 5:1 to 1:5.

Also preferably, said compound comprising an amine moiety has a molecular weight below 300 g/mol. Also preferably, said compound comprising an amine moiety has a molecular weight below 150 g/mol. More preferably, said compound comprising an amine moiety is a primary amine. Even more preferably, said compound comprising an amine moiety is an alkanolamine. Even more preferably, said compound comprising an amine moiety is a tertiary amine.

According to a preferred embodiment of the present invention, the alkanolamine is selected from the group consisting of: monoethanolamine; diethanolamine; triethanolamine; and combinations thereof. Preferably, alkanolamine is triethanolamine.

According to a preferred embodiment of the present invention, the compound comprising a sulfonic acid moiety is selected from the group consisting of: alkylsulfonic acids where the alkyl groups range from C1-C6 and are linear or branched; and combinations thereof. Preferably, said compound comprising a sulfonic acid moiety is selected from the group consisting of: methanesulfonic acid; ethanesulfonic acid; propanesulfonic acid; 2-propanesulfonic acid; isobutylsulfonic acid; t-butylsulfonic acid; butanesulfonic acid; iso-pentylsulfonic acid; t-pentylsulfonic acid; pentanesulfonic acid; t-butylhexanesulfonic acid; and combinations thereof. More preferably, said compound comprising a sulfonic acid moiety is methanesulfonic acid.

According to an aspect of the present invention, there is provided an aqueous composition for use in the delignification of biomass such as wood, wherein said composition comprises:
  sulfuric acid;
  a compound comprising an amine moiety;
  a compound comprising a sulfonic acid moiety; and
  a peroxide.
wherein the sulfuric acid, the compound comprising an amine moiety; and the compound comprising a sulfonic acid moiety are present in a mole ratio ranging from 2:1:1 to 30:1:1.

According to an aspect of the present invention, there is provided an aqueous composition for use in the breaking down of cellulose from biomass (i.e., a plant source), wherein said composition comprises:
  sulfuric acid in a 20-70 wt % of the total weight of the composition;
  a compound comprising an amine moiety;
  a compound comprising a sulfonic acid moiety; and
  a peroxide;
wherein the sulfuric acid, the compound comprising an amine moiety; and the compound comprising a sulfonic acid moiety are present in a mole ratio ranging from 2:1:1 to 30:1:1.

Preferably, the peroxide is hydrogen peroxide.

According to an aspect of the present invention, there is provided a method of delignification of biomass/plant material, said method comprising:
  providing said plant material comprising cellulose fibers and lignin;
  exposing said plant material requiring to a composition comprising:
    sulfuric acid in a 20-70 wt % of the total weight of the composition;
    a compound comprising an amine moiety;
    a compound comprising a sulfonic acid moiety;
  for a period of time sufficient to remove substantially all of the lignin present on said plant material.

Preferably, the composition further comprises a peroxide.

Preferably, the compound comprising a sulfonic acid moiety is selected from the group consisting of: alkylsulfonic acids where the alkyl groups range from C1-C6 and are linear or branched; and combinations thereof. Preferably, said compound comprising a sulfonic acid moiety is selected from the group consisting of: methanesulfonic acid; ethanesulfonic acid; propanesulfonic acid; 2-propanesulfonic acid;

isobutylsulfonic acid; t-butylsulfonic acid; butanesulfonic acid; iso-pentylsulfonic acid; t-pentylsulfonic acid; pentanesulfonic acid; t-butylhexanesulfonic acid; and combinations thereof. More preferably, said compound comprising a sulfonic acid moiety is methanesulfonic acid.

Preferably, said compound comprising an amine moiety has a molecular weight below 300 g/mol.

More preferably, said compound comprising an amine moiety has a molecular weight below 150 g/mol. According to a preferred embodiment of the present invention, the composition has a pH less than 1. According to another preferred embodiment of the present invention, the composition has a pH less than 0.5.

The inventors have discovered that delignification of biomass such as wood material/woody pulp (for example, but not limited to wood chips) can occur at substantially lower temperatures than those used during conventional kraft pulping process. In fact, experiments conducted at room temperature with preferred compositions according to the present invention were shown to degrade the lignin present in wood chips to free up cellulose fibers. According to a preferred embodiment of a method according to the present invention, a wood sample was dissolved at 30° C. upon exposure to a composition according to a preferred embodiment of the present invention. According to a preferred embodiment of the present invention, one could substantially reduce the energy input costs involved in current pulp delignification by applying a method involving a preferred composition of the present invention.

4. BRIEF DESCRIPTION OF THE FIGURES

Figure 2:

The invention may be more completely understood in consideration of the following description of various embodiments of the invention in connection with the accompanying figure, in which:

FIG. 1 is a photograph of the dissolution of a wood chip in a composition according to the present invention where the time elapsed was 1 minute; and FIG. 2 is a photograph of the dissolution of a wood chip in a composition according to the present invention) where the time elapsed was 24 hours.

5. DESCRIPTION OF THE INVENTION

The experiments carried out using an aqueous acidic composition according to a preferred embodiment of the present invention as shown that wood chips can undergo delignification under controlled reaction conditions and eliminate or at least minimize the degradation of the cellulose. Degradation is understood to mean a darkening of cellulose or carbonization (conversion to carbon black) which is symbolic of an uncontrolled acid attack on the cellulose and staining thereof.

Preferably, the compound comprising an amine moiety and the compound comprising a sulfonic acid moiety are present in a 1:1 ratio. Together in the presence of sulfuric acid, there seems to be a coordination of the compounds which acts as a modified sulfuric acid. In that respect, it is believed that the presence of a sulfonic acid group along with an amine group form part of this modified acid. The strength of the modified acid is dictated by the moles of sulfuric acid to the moles of the compound comprising an amine moiety and the compound comprising a sulfonic acid moiety. Hence, a composition comprising a molar ratio of 6:1:1 of sulfuric acid:the compound comprising an amine moiety:the compound comprising a sulfonic acid moiety would be much less reactive than a composition of the same components in a 28:1:1 molar ratio. It was also noted that the ratio between the compound comprising an amine moiety and the compound comprising a sulfonic acid moiety can vary from 0.5:1 and 2:1 without having a noticeable impact on the reactivity of the entire composition, i.e., when put in the presence of sulfuric acid.

When performing delignification of wood using a composition according to a preferred embodiment of the present invention, the process can be carried out at substantially lower temperatures than temperatures used in the conventional kraft pulping process. The advantages are substantial, here are a few: the kraft pulping process requires temperatures in the vicinity of 176-180° C. in order to perform the delignification process, a preferred embodiment of the process according to the present invention can delignify wood at far lower temperatures, even as low as 20° C. According to a preferred embodiment of the present invention, the delignification of wood can be performed at temperatures as low as 0° C. According to a preferred embodiment of the present invention, the delignification of wood can be performed at temperatures as low as 10° C. According to a preferred embodiment of the present invention, the delignification of wood can be performed at temperatures as low as 30° C. According to another preferred embodiment of the present invention, the delignification of wood can be performed at temperatures as low as 40° C. According to yet another preferred embodiment of the present invention, the delignification of wood can be performed at temperatures as low as 50° C. According to yet another preferred embodiment of the present invention, the delignification of wood can be performed at temperatures as low as 60° C. Other advantages include: a lower input of energy; reduction of emissions and reduced capital expenditures; reduced maintenance; lower shut down/turn around costs; also there are HSE advantages compared to conventional kraft pulping compositions.

In each one of the above preferred embodiments, the temperature at which the processes are carried out are substantially lower than the current energy-intensive kraft process.

Moreover, the kraft process uses high pressures to perform the delignification of wood which is initially capital intensive, dangerous, expensive to maintain and has high associated turn-around costs. According to a preferred embodiment of the present invention, the delignification of wood can be performed at atmospheric pressure. This, in turn, circumvents the need for highly specialized and expensive industrial equipment such as pressure vessels/digestors. It also allows the implementation of delignification units in many of parts of the world where the implementation of a kraft plant would previously be impracticable due to a variety of reasons.

Some of the advantages of a process according to a preferred embodiment of the present invention, over a conventional kraft process are substantial as the heat/energy requirement for the latter is not only a great source of pollution but is in large part the reason the resulting pulp product is so expensive and has high initial capital requirements. The energy savings in the implementation of a process according to a preferred embodiment of the present invention would be reflected in a lower priced pulp and environmental benefits which would have both an immediate impact and a long-lasting multi-generational benefit for all.

Further cost savings in the full or partial implementation of a process according to a preferred embodiment of the present invention, can be found in the absence or minimization of restrictive regulations for the operation of a high temperature and high-pressure pulp digestors.

6. EXAMPLES

A preferred embodiment of the composition according to the present invention was tested to determine its power to delignify a wood chip.

The experiments were completed using approximately 0.2 g of wood and approximately 20 g of solution. The mixtures were stirred at 200 rpm at a temperature of 30° C.

FIGS. 1 and 2 show the dissolution of two wood chips in the presence of a composition according to a preferred embodiment of the present invention. The composition according to the preferred embodiment in question comprises sulfuric acid and monoethanolamine and methanesulfonic acid in a ratio of 6:1:1. It is noteworthy to mention that the solution is still clear after 1 minute (see FIG. 1). A sulfuric acid composition would already have shown signs of discoloration which is indicative of cellulose degradation to carbon black. In fact, the solution remains clear during the entire experiment which lasted up to 24 hours (see FIG. 2). After 24 hours, the solution has managed to dissolve all of the lignin present in the wood chip while maintaining the packets of crystalline cellulose intact (or substantially intact). This is evidence of a mild oxidizing composition which specifically targets lignin while sparing the cellulose.

The above experiment is a clear indication that a preferred composition according to the present invention not only provides an adequate dissolving acid to delignify plant material but is also valuable in controlling the ultimate degradation of cellulosic material into carbon black residue resulting in higher yields potentially for the operators thus increasing profitability while reducing emissions and the risk to the employees, contractors and public.

6.1. ADDITIONAL DELIGNIFICATION EXPERIMENTS

Sulfuric acid, methanesulfonic acid (MSA), triethanolamine (TEOA) and hydrogen peroxide were mixed with increasing MSA and TEOA concentrations and reacted with biomass (wood chips) overnight at ambient conditions to assess the effectiveness of the variation on the molar ratios on the extent of reaction. Control tests were run for the respective mixtures with just kraft lignin or just cellulose added instead of biomass. Commercially available lignin (Sigma-Aldrich; Lignin, kraft; Prod #471003) was used as a control in the testing. Commercially cellulose (Sigma-Aldrich; Cellulose, fibers (medium); Prod #C6288) was also used as a control in the testing.

The solid phase of each blend was filtered off after 20 h reaction time, rinsed with water and dried in an oven at 45° C. to constant weight. An effective blend should dissolve all lignin and leave the cellulose as intact as possible. The results of the experiments are reported in Table 1 below.

TABLE 1

Recovery of solids (% of initial mass) after 20 h reaction time

| Blend | Wood (wt % remaining after reaction) | Lignin control (wt % remaining after reaction) | Cellulose control (wt % remaining after reaction) |
| --- | --- | --- | --- |
| 28:1:1:28 | 43.21 | 0.00 | 43.21 |
| 10:1:1:10 | 47.13 | 0.00 | 88.63 |
| 2:1:1:2 | 54.65 | 21.74 | 91.92 |

A blend with a ratio of 28:1:1:28 of sulfuric acid (96% conc. used) to MSA to TEOA to hydrogen peroxide (as 30% solution) results in a mass recovery of 43% from wood and cellulose. This shows that the acid/peroxide mixture is too aggressive and depolymerizes too much of the cellulose. None of the lignin could be recovered, which is the required result. When the concentration of the retardant mix of MSA/TEOA is increased to a tenth of the acid and peroxide concentration, still all of the lignin is depolymerized enough to go into solution. However, the cellulose is not attacked as much anymore. 89% of the cellulose could be recovered with this blend. Increasing the retardant concentration to half the acid/peroxide concentration slows down the biomass digestion to an extent which is much less desirable. 55% of the wood mass and 92% of the cellulose could be recovered, but also 22% of the lignin was not brought into solution.

6.2. BATCH PROCESS USING A BLEND OF $H_2SO_4$:TEOA:MSA:$H_2O_2$ IN A MOLAR RATIO OF 10:1:1:10

A batch process was carried out in order to scale up the compositions and process discussed previously. For the preparation of a batch process, 3,409 g sulfuric acid (93%) was placed in a large glass reactor (101) and 444 g methanesulfonic acid (70%) and 482 g triethanolamine were added. The mixture was stirred at 100 RPM. Then 3,665 g hydrogen peroxide solution (29%) was slowly added (over 1 to 1.5 hours) to the modified acid. The reactor was chilled to dissipate the generated heat so that the temperature of the blend does not exceed 40° C. After addition of the hydrogen peroxide the reactor system was left to equilibrate to ambient temperature (30 minutes). The molar blend ratio (in order of addition) was 10:1:1:10. 400 g of unsized wood shavings (sawdust) was slowly added to the reactor. The temperature rise was monitored. When the reactor temperature reached 55° C., the reactor was chilled to a temperature of 26° C. After this, cooling was no longer necessary. The reaction was carried out for 20 h, then the reaction mixture was transferred to a filter system with a 20 μm Teflon filter sheet. The filtrate was discarded and the remaining filter cake washed with 12 l of water until the runoff reached a pH value of about 6. The filter cake was the oven dried (45° C.) overnight. The cellulose yield compared to added biomass was 43.2%.

The hydrocarbon content of the resulting cellulose was determined to be 94.4% which is close to the Sigma-Aldrich cellulose lot #WXBC9745V—95.7% standard used as a comparison. The water content was determined to be 1.70% which is close to the Sigma-Aldrich cellulose lot #WXBC9745V—3% standard used as a comparison. The Kappa #=0, which means that there is no lignin left in the sample. X-ray diffraction was carried out on the sample and indicated that apparent crystallinity was of 58.2% which is in line with our previously tested numbers and the commercial cellulose from Aldrich was measured to be 62.9%. Scanning electron microscopy was carried out shows a material very high fiber content.

A method to yield glucose from wood pulp would represent a significant advancement to the current process where the conversion of such is chemical and energy intensive, costly, emissions intensive and dangerous all while not resulting in highly efficient results, especially in large-scale operations. It is desirable to employ a composition which may delignify wood but also allows the operator some control in order to preserve the cellulose rather than degrading it to carbon black resulting in higher efficiencies and yields along with increased safety and reduced overall costs.

According to a preferred embodiment of the method of the present invention, the separation of lignin can be effected and the resulting cellulose fibers can be further processed to yield glucose monomers. Glucose chemistry has a multitude of uses including as a starting block in the preparation of widely used chemicals including but not limited to diacetonide, dithioacetal, glucoside, glucal and hydroxyglucal to name but a few.

According to another preferred embodiment of the present invention, the composition can be used to decompose organic material by oxidation such as those used in water treatment, water purification and/or water desalination. An example of this is the removal (i.e. destruction) of algae on filtration membranes. As such membranes can be quite expensive, it is imperative that they be used for as long as possible. However, given the difficulty to remove organic matter which accumulates on it over time, new approaches are necessary to do so efficiently and with as little damage to the membrane as possible. Mineral acids are too strong and, while they will remove the organic matter, will damage the filtration membranes. A preferred composition of the present invention remedies this issue as it is less aggressive than the mineral acids and, as such, will remove the organic contaminants in a much milder approach, therefore sparing the membrane.

While the foregoing invention has been described in some detail for purposes of clarity and understanding, it will be appreciated by those skilled in the relevant arts, once they have been made familiar with this disclosure that various changes in form and detail can be made without departing from the true scope of the invention in the appended claims.

The invention claimed is:

1. An aqueous acidic composition comprising:
   sulfuric acid;
   a compound comprising an amine moiety;
   a compound comprising a sulfonic acid moiety; and
   a peroxide;
   wherein said composition has a pH of less than 1, and
   wherein said sulfuric acid, said compound comprising an amine moiety, and said compound comprising a sulfonic acid moiety are present in the composition in a molar ratio ranging from 28:1:1 to 2:1:1.

2. The composition according to claim 1, wherein said compound comprising an amine moiety has a molecular weight of less than 300 g/mol.

3. The composition according to claim 1, wherein said compound comprising an amine moiety is a primary amine.

4. The composition according to claim 1, wherein said compound comprising an amine moiety is an alkanolamine.

5. The composition according to claim 1, wherein said compound comprising an amine moiety is a tertiary amine.

6. The composition according to claim 1, wherein said compound comprising an amine moiety is an alkanolamine selected from the group consisting of monoethanolamine, diethanolamine, triethanolamine, and combination of any two or more therefrom.

7. The composition according to claim 1, wherein said compound comprising an amine moiety is triethanolamine.

8. The composition according to claim 1, wherein said compound comprising a sulfonic acid moiety is an alkylsulfonic acid selected from the group consisting of alkylsulfonic acids, wherein the alkyl is a linear or branched C1-C6 alkyl, and combination of any two or more therefrom.

9. The composition according to claim 1, wherein said compound comprising a sulfonic acid moiety is an alkylsulfonic acid selected from the group consisting of methanesulfonic acid, ethanesulfonic acid, propanesulfonic acid, 2-propanesulfonic acid, isobutylsulfonic acid, t-butylsulfonic acid, butanesulfonic acid, iso-pentylsulfonic acid, t-pentylsulfonic acid, pentanesulfonic acid, t-butylhexanesulfonic acid, and combination of any two or more therefrom.

10. The composition according to claim 1, wherein said compound comprising a sulfonic acid moiety is methanesulfonic acid.

11. An aqueous composition comprising:
   sulfuric acid present in the composition in an amount ranging from 20-70 wt % of the total weight of the composition;
   a compound comprising an amine moiety;
   a compound comprising a sulfonic acid moiety; and
   a peroxide;
   wherein said composition has a pH of less than 1,
   wherein said sulfuric acid, said compound comprising an amine moiety, and said compound comprising a sulfonic acid moiety are present in the composition in a molar ratio ranging from 2:1:1 to 28:1:1, and
   wherein said composition is suitable for processing and depolymerizing cellulose in a plant source.

* * * * *